United States Patent [19]

Zabotto et al.

[11] Patent Number: 4,673,526

[45] Date of Patent: Jun. 16, 1987

[54] ANHYDROUS SKIN CLEANSING COMPOSITION CONTAINING AN OIL PHASE, AN EMULSIFYING AGENT AND PARTICULATE WATER SOLUBLE POLYMERIC ABRASIVE PARTICLES

[75] Inventors: Arlette Zabotto, Paris; Jean-Claude Contamin, Chilly Mazarin, both of France

[73] Assignee: Societe Anonyme dite: L'Oreal, Paris, France

[21] Appl. No.: 734,139

[22] Filed: May 15, 1985

[30] Foreign Application Priority Data

May 15, 1984 [FR] France ................... 84 07487

[51] Int. Cl.$^4$ ................... C11D 1/78; C11D 3/37
[52] U.S. Cl. ................... 252/174.16; 252/89.1; 252/174.17; 252/174.23; 252/174.24; 252/546; 252/174.21; 252/DIG. 2; 252/DIG. 5; 252/DIG. 14
[58] Field of Search ............. 252/89.1, 174.17, 174.23, 252/174.24, 164, DIG. 5, DIG. 2, DIG. 14, 174.21, 174.16, 546; 514/846, 781; 424/78, 81

[56] References Cited

U.S. PATENT DOCUMENTS

| | | | |
|---|---|---|---|
| 3,146,170 | 8/1964 | Battista | 252/174.17 |
| 3,277,013 | 10/1966 | Gianladis | 252/153 |
| 3,645,904 | 2/1972 | Beach | 252/174.23 |
| 3,795,624 | 3/1974 | Harry | 252/91 |
| 3,819,525 | 6/1974 | Hattenbrun | 252/132 |
| 4,035,514 | 7/1977 | Davis | 424/365 |
| 4,048,123 | 9/1977 | Hramchenko et al. | 252/545 |
| 4,155,870 | 5/1979 | Jorgensen | 252/131 |
| 4,440,745 | 4/1984 | Schmidt et al. | 424/78 |
| 4,460,488 | 7/1984 | Grollier et al. | 252/89.1 |
| 4,488,564 | 12/1984 | Grollier et al. | 132/7 |
| 4,495,079 | 1/1985 | Good | 252/106 |
| 4,537,604 | 8/1985 | Dawson | 51/298 |
| 4,557,853 | 12/1985 | Collins | 252/128 |

FOREIGN PATENT DOCUMENTS 1322144 2/1963 France .
2033292 12/1970 France .
2085692 12/1971 France .
2168102 8/1973 France .

*Primary Examiner*—Prince E. Willis
*Attorney, Agent, or Firm*—Cushman, Darby & Cushman

[57] ABSTRACT

This compound contains an oily phase, at least one emulsifying agent and at least one abrasive substance, said compound being presented in anhydrous form and said abrasive substance, in suspension in the oily phase, being highly hydrosoluble and with an average particle size between 50 and 1000 microns. This compound allows the deep cleansing of the skin through exfoliant action.

11 Claims, No Drawings

ANHYDROUS SKIN CLEANSING COMPOSITION CONTAINING AN OIL PHASE, AN EMULSIFYING AGENT AND PARTICULATE WATER SOLUBLE POLYMERIC ABRASIVE PARTICLES

This invention pertains to a cosmetic composition designed for skin cleansing to remove oily particles and dead cells present on the epidermis.

The skin of the human body and more specifically facial skin periodically needs a deep cleansing to remove not only the oily particles resulting from secretions, but also dead skin caused by desquamation of the epidermis.

An exfoliant cleansing or "peeling" promotes the partial regeneration of epidermal tissues, restoring the skin's freshness and suppleness and favoring the application and the penetration of cosmetics or dermo-pharmaceutical products.

The cleansing of the skin can be achieved utilizing detergent solutions, but these have a tendency to cause pronounced drying of the skin without completely removing foreign matter.

There have also been proposed, to effect the exfoliation of the epidermis, compositions in the form of creams containing abrasive substances comprised of insoluble particles, in the appropriate size and shape, such as, for example, quartz particles, which, after application to the parts of the body to be cleansed, are removed by wiping or rinsing with water.

Such compositions are particularly effective but highly irritating. In addition, particles of the abrasive materials can remain in the pores of the skin and thus cannot be totally removed.

More recently, one has also advocated, for the cleansing of skin, especially oily skin, aqueous compositions in the form of creams, which contain abrasives in the form of mineral substances or sugars with low hydrosolubility in the cream, but which can dissolve during the cleansing of the skin with water.

Because the purpose of these compositions is to eliminate oily substances, these products are generally devoid of such products, but when they do contain them, they are present in a proportion less than about 5% by weight.

Since the abrasive particles have low hydrosolubility, their removal during rinsing with water is often slow and never complete.

Moreover, the compositions, by drying on the skin, present the inconvenience of not allowing a prolonged massage which is necessary to obtain a proper exfoliant action.

At present, it has just been noted that it was possible to achieve excellent cleansing compositions which leave the skin fresh and clean, totally free from oils, dirt and dead skin, by applying an anydrous composition to the skin and massaging; this composition containing, in an oily phase, an emulsifying agent and highly hydrosoluble abrasive agents.

With one of the of the purposes of the cleansing composition being the removal of oily substances on the skin, the media for the compositions proposed up to now do not contain fat bodies, or have only a relatively low concentration of them, to avoid any addition of oils to the skin.

The compositions, according to the invention, on the other hand, are essentially characterized by the presence of a significant oil phase, comprised of at least one oil or a mixture of an oil and/or at least one wax promoting a gentle and prolonged massage of the body, notably of the face, with the aid of the abrasive material and which disappears completely when rinsed with water, leaving the skin particularly clean and soft.

The compositions of the present invention do not dry, thus allowing a prolonged massage, and remain thick or oily as long as water is not added. The lubricating effect of the compositions also makes the massage much gentler and more comfortable than with the presently known compositions.

The proper removal and the cosmetic properties of the compositions of the present invention are obtained through the combined effect of the chosen emulsifying agent and the particles which, under the action of the rinsing water, become soluble, while lubricating the skin.

This invention, as a new industrial product, pertains to a cosmetic composition for the cleansing of the skin, containing, in an oily phase, at least one emulsifying agent and at least one abrasive substance, in suspension in the oily phase, being a highly hydrosoluble polymeric compound, with the average size of the particles being between 50 and 1000 microns.

The viscosity of the cleansing compounds is generally between 1 and 200 poises, preferably between 1.5 and 150 poises.

They are in liquid form when the viscosity is between 1 and 5 poises or in gel form when viscosity is between 5 and 200 poises.

The oily phase is comprised of an oil, a mixture of oils, or a mixture of at least one oil and at least one wax, and is present at a concentration between 50 and 95% with respect to the total weight of the composition.

Among the oils which can constitute the oil phase, the following can be cited:

1. Mineral oils: paraffin oil, petroleum jelly oil and mineral oils with a boiling point between 310 and 410 degrees C.,
2. Animal oils: Purcellin oil and perhydrosqualene,
3. Vegetable oils: sweet almond oil, palm oil, Calophyllum oil, avocado oil, olive oil, castor oil, cereal germ oil, such as oil of wheat germs,
4. Silicone oils: dimethylpolysiloxane,
5. Synthesis esters: butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, di-caprylate of proplyene glycol, di-isopropyl adipate.
6. The organic alcohols: oleic alcohol, linoleic alcohol, linolenic alcohol, isostearyl alcohol, octyl dodecanol,
7. The esters derived from lanolic acid: isopropyl lanolate, isocetyl lanolate.

In addition to the classes of the compounds mentioned above, one can also utilize as oils the acetyl glycerides, the octanoates and decanoates of alcohols and polyalcohols such as those of glycol and glycerol, the ricinoleates of alcohols and polyalcohols such as that of cetyl.

When the oily phase contains at least one wax, the ratio of oil or oil mixture to wax is generally 1:1 to 3:1.

Among these waxes, the following can be mentioned:

1. The mineral waxes: microcrystalline waxes, paraffin, petroleum jelly,
2. The fossil waxes: ozokerite, montan wax,
3. Animal waxes: beeswax, spermaceti, lanolin wax, lanolin derivatives such as lanolin alcohols, hydrogenated lanolin, hydroxylated lanolin, acetylated lanolin, fatty acids of lanolin, acetylated lanolin alcohol, 4. Vegetable waxes: candellila wax, carnauba wax, sumac wax, cocoa butter wax, 5. Hydrogenated waxes which are solid at 25 degrees C.: hydrogenated castor oil, hydrogenated palm oil, hydrogenated tallow, hydrogenated cocoa oil, hydrogenated soy oil, 6. Synthetic oils: polyethylene, copolymerized polyethylene waxes.

7. The fatty esters which are solid at 25 degrees C.: monomyristate of propylene glycol, myristyl myristate, 8. Silicone oils: methyloctadecane-oxypolysiloxane and poly(dimethylsiloxy)stearoxysiloxane, Among the waxes, the following compounds can also be utilized:

Cetyl alcohol, stearyl alcohol, the mono-, di- and tri-glycerides which are solid at 25 degrees C., stearic monoethenolamide, colophane and its derivatives such as abietates of glycol and glycerol, the surroglycerides and oleates, myristates, lanolates, stearates and dihydroxy stearates of calcium, magnesium, zinc and aluminum.

According to a preferred production formula for the invention, the oily phase is comprised of petroleum jelly oil or a mixture of petroleum jelly oil and another oil, possibly mixed with at least one wax.

The emulsifiers must be oleosoluble, i.e., miscible in the oily phase and able to emulsify at the surrounding temperature when the product is rinsed with water.

According to the invention, the emulsifying agent is present in the compositions at a concentration between 1 and 30% and preferably between 3 and 25% with respect to the total weight of the composition.

The emulsifying agents which are especially preferred and which have yielded highly satisfactory results are:

(1) egg or soy lecithin, (2) ether poyglycerol alkyls such as those described in French Pat. No. 71.17206 and notably the product resulting from the condensation of 7 moles of glycidol on a C18 2-diol, (3) The glycerol stearates, notably those sold under the commercial name WITCONOL MST by the WITCO Company, or under the commercial name SIMUSOL 165 by the SEPPIC Company, (4) The esters of sorbitan and fatty acids, in particular, the oleates of sorbitan such as the mono-oleate of sorbitan sold under the commercial name of ARLACEL 80 or the trioleate of sorbitan sold under the commercial name of ARLACEL 85 by the ATLAS Company.

(5) The polyoxyethylenated fatty alcohols, said fatty alcohols containing 12 to 18 carbon atoms, in particular, lauryl alcohol polyoxethylenated with 4 moles of ethylene oxide, sold under the commercial name of BRIJ 30 by the ATLAS Company, (6) The esters of phosphoric acid and ethoxylated fatty acids such as the product sold by the HOECHST Company under the commercial name of HOSTAPHAT 340 N.

The abrasive solid particles, which are highly hydrosoluble and which allow a deep and perfect cleansing of the skin must have an appropriate granulometry allowing a gentle and non-irritating action, the average size of the particles being generally between 50 and 1000 microns and preferably between 75 and 400 microns.

Obviously, these abrasive particles must be totally insoluble in the oily phase during which they remain in suspension.

As indicated above, these solid abrasive particles must be highly hydrosoluble so that, when rinsed with water, they rapidly become soluble, forming an emulsion with the consistency of a cream or gel.

The utilization of the highly hydrosoluble solid particles thus allows the correction of the drawbacks of the known compositions, the bases of which are insoluble substances such as silica or low-hydrosolubles such as alkaline metal salts and sugars.

In the compositions according to the invention, the solid hydrosoluble particles of the abrasive substance are generally present at a concentration between 1 and 10% and preferably between 2 and 5%.

Among the specifically preferred abrasive substances which respond to the above conditions, one can cite:

1. The xanthane gums, which are heteropolysaccharides of high molecular weight, greater than 1 million, notably the products known under the commercial names of KELTROL and KELTROL F by the KELCO Company, with respective average particle sizes 180 and 75 microns, as well as the product known under the commercial name of "RHODOPOL 23" sold by the Rhone-Poulenc Company, with an average particle size of 80 microns, 2. The carboxymethylamidons, notably the product sold under the commercial name of PERFECTAMYL CMA ZK N by the AVEBE Company, with an average particle size under about 125 microns, 3. The cellulose ethers such as ethylhydroxyethylcellulose, sold under the commercial name of "BERMOCOLL" by the BEROL CHIMIE Company, of which 95% of the particles have an average size under 500 microns, 4. The hydroxyalkylcelluloses such as hydroxyethylcellulose and hydroxypropylmethylcellulose, sold under the commercial name of CELLOSIZE by the UNION CARBIDE Company, and which have an average particle size of 70 microns, or under the commercial name of NATROSOL by the HERCULES Company and which have an average particle size of 50 microns, or under the commercial name of METHOCEL by the DOW CHEMICAL Company, including METHOCEL E50, with an average particle size greater than 50 microns.

5. The copolymers of acrylic acid and acrylamide with an average molecular weight between 9 and 12 million, notably the product sold under the commercial name of HERCOFLOC 1031 by the HERCULES Company, with an average particle size of 160 microns.

The compositions according to the invention can also contain other substances which are supplementary ingredients, such as, for example, fragrances, coloring substances, preservatives, keratolytic substances, antioxidizing agents, etc . . . .

To effect the cleansing of the skin, notably of the facial skin, a sufficient amount of a composition according to the invention is applied and subsequently massaged, preferably in a circular manner. Thus a moderate abrasion is achieved, without irritation or the appearance of redness.

After massaging, the composition is removed, along with the dead skin debris and other residue, by a generous application of water, which allows the emulsification of the composition and allows the abrasive particles to become soluble, while giving the skin a clean and supple appearance.

Since the abrasive particles are soluble, their removal is perfect and promotes a better consistency of the composition during rinsing.

To provide a better understanding of the invention, several examples of cleansing compositions will be given, as an illustration and with no limitative nature whatsoever:

EXAMPLE 1

According to the invention, an exfoliant body oil containing the following ingredients is prepared:
Oily egg yolk extract containing egg lecithin: 70.00 g
Corn germ oil: 26.35 g
RHODOPOL 23 C: 3.00 g
methyl p-hydroxybenzonate: 0.20 g
Fragrance: 0.40 g
Butylhydroxyanisol: 0.05 g.

EXAMPLE 2

According to the invention, a facial cleansing gel containing the following ingredients is prepared:
polyglycerol alkylether obtained by the condensation of 7 moles of glycidol on a C18 2-diol: 10.00 g
ALCOLEC 4135 (sold by the AMERICAN LECITHIN Company, lecithin-based mixture with sorbitan esters and propylene glycol esters): 9.00 g
Petroleum jelly oil: 78.25 g
KELTROL F (xanthane gum): 2.00 g
methyl and propyl p-hydroxybenzoate: 0.25 g
Fragrance: 0.50 g.

EXAMPLE 3

According to the invention, a gentle cleansing cream containing the following ingredients is prepared:
ALCOLEC 4135: 9.00 g
Alkylether of polyglycerol obtained through condensation of 7 moles of glycidol on a C18 2-diol: 9.00 g
Keltrol F: 2.00 g
Magnesium stearate: 10.00 g
Petroleum jelly oil: 69.25 g
Methyl and propyl p-hydroxybenzoate: 0.25 g
Fragrance: 0.50 g.

EXAMPLE 4

A cleansing cream for the body containing the following ingredients is prepared:
WITCONOL MST: 6.00 g
Polyglycerol Alkylether obtained by condensation of 7 moles of glycidol on a C18 2-diol: 14.00 g
PERFECTAMYL CMA ZKN: 4.00 g
Petroleum jelly oil: 75.25 g
Methyl p-hydroxybenzoate: 0.25 g
Fragrance: 0.50 g.

EXAMPLE 5

A facial cleansing gel containing the following ingredients is prepared:
HOSTAPHAT KW 340 N: 14.00 g
ALCOLEC 4135: 6.00 g
Petroleum jelly: 6.00 g
Ozokerite: 2.00 g
Petroleum jelly oil: 68.40 g
HERCOFLOC 1031: 3.00 g
Preservative (IRGASAN DP 300): 0.10 g
Fragrance: 0.50 g.

We claim:

1. An anhydrous skin cleansing composition comprising from 50 to 95 percent by weight based on the total weight of said composition of an oily phase, from 1 to 30 weight percent based on the total weight of said composition of an emulsifying agent and from 1 to 10 weight percent based on the total weight of said composition of a water-soluble polymeric particulate abrasive substance, said abrasive substance having an average particle size ranging from 50 to 1,000 microns and said composition having a viscosity ranging from 1 to 200 poises.

2. The composition of claim 1 having a viscosity ranging from 1.5 to 150 poises.

3. The composition of claim 1 wherein said oily phase comprises an oil, a mixture of oils or a mixture of at least one oil and at least one wax.

4. The composition of claim 1 wherein said emulsifying agent is present in an amount ranging from 3 to 25 weight percent based on the total weight of said composition.

5. The composition of claim 1 wherein said emulsifying agent is selected from the group consisting of egg lecithin, soy lecithin, a polyglycerol alkyl ether, a glycerol stearate, an ester of sorbitan with a fatty acid, a polyoxyethylenated fatty acid and an ester of phosphoric acid with an ethoxylated fatty acid.

6. The composition of claim 1 wherein said particulate abrasive substance is present in an amount ranging from 2 to 5 weight percent based on the total weight of said composition.

7. The composition of claim 1 wherein said particulate abrasive substance is selected from the group consisting of a xanthane gum, a carboxymethylamidon, a cellulose ether, a hydroxyalkyl cellulose and a copolymer of acrylic acid and acrylamide.

8. The composition of claim 1 which also includes at least one of a fragrance, a coloring substance, a preservative, a keratolytic agent or an antioxidizing agent.

9. An anhydrous skin cleansing composition comprising an oily phase, at least one emulsifying agent and at least one water-soluble polymeric particulate abrasive substance,
said oily phase being present in an amount ranging from 50 to 95 percent by weight based on the total weight of said composition and comprising an oil, a mixture of oils or a mixture of at least one oil and at least one wax,
said emulsifying agent being present in an amount ranging from 1 to 30 weight percent based on the total weight of said composition and being selected from the group consisting of egg lecithin, soy lecithin, a polyglycerol alkyl ether, a glycerol stearate, an ester of sorbitan with a fatty acid, a polyoxyethylenated fatty acid and an ester of phosphoric acid with an ethoxylated fatty acid, and
said particulate abrasive substance (1) being present in an amount ranging from 1 to 10 weight percent based on the total weight of said composition, (2) having a particle size ranging from 50 to 1,000 microns and (3) being selected from the group consisting of a xanthane gum, a carboxymethylamidon, a cellulose ether, a hydroxyalky cellulose and a copolymer of acrylic acid and acrylamide.

10. A process for cleansing the skin comprising applying to said skin an effective amount of an anhydrous skin cleansing composition comprising from 50 to 95 percent by weight based on the total weight of said composition of an oily phase, from 1 to 30 weight percent based on the total weight of said composition of an emulsifying agent and from 1 to 10 weight percent based on the total weight of said composition of a water-soluble polymeric particulate abrasive substance, said abrasive substance having an average particle size ranging from 50 to 1,000 microns and said composition having a viscosity ranging from 1 to 200 poises, massaging the skin with said composition, and thereafter applying water to said skin to remove said composition.

11. A process for cleansing the skin comprising applying to said skin an effective amount of an anhydrous skin cleansing composition comprising an oily phase, an emulsifying agent and a water-soluble polymeric particulate abrasive substance, said oily phase being present in an amount ranging from 50 to 95 percent by weight based on the total weight of said composition and comprising an oil, a mixture of oils or a mixture of at least one oil and at least one wax, said emulsifying agent being present in an amount ranging from 1 to 30 weight percent based on the total weight of said composition and being selected from the group consisting of egg lecithin, soy lecithin, a polyglycerol alkyl ether, a glycerol stearate, an ester of sorbitan with a fatty acid, a polyoxyethylenated fatty acid and an ester of phosphoric acid with an ethoxylated fatty acid, and said particulate abrasive substance (1) being present in an amount ranging from 1 to 10 weight percent based on the total weight of said composition (2) having a particle size ranging from 50 to 1,000 microns and (3) being selected from the group consisting of a xanthane gum, a carboxymethylamidon, a cellulose ether, an hydroxyalkyl cellulose and a copolymer of acrylic acid and acrylamide, massaging the skin with said composition and thereafter applying water to said skin to remove said composition.

* * * * *